United States Patent
Beraud

(10) Patent No.: US 9,555,142 B2
(45) Date of Patent: Jan. 31, 2017

(54) METHOD AND APPARATUS FOR HEAT TREATMENT OF WASTE

(76) Inventor: Christophe Beraud, Orange (FR)

(*) Notice: Subject to any disclaimer, the term of this patent is extended or adjusted under 35 U.S.C. 154(b) by 150 days.

(21) Appl. No.: 14/235,053

(22) PCT Filed: Jul. 24, 2012

(86) PCT No.: PCT/FR2012/051753
§ 371 (c)(1),
(2), (4) Date: Jan. 25, 2014

(87) PCT Pub. No.: WO2013/014387
PCT Pub. Date: Jan. 31, 2013

(65) Prior Publication Data
US 2014/0294669 A1 Oct. 2, 2014

(30) Foreign Application Priority Data
Jul. 26, 2011 (FR) ...................................... 11 56794

(51) Int. Cl.
*A61L 2/04* (2006.01)
*A61L 11/00* (2006.01)
*B09B 3/00* (2006.01)

(52) U.S. Cl.
CPC .................. *A61L 2/04* (2013.01); *A61L 11/00* (2013.01); *B09B 3/0075* (2013.01); *B09B 3/0083* (2013.01)

(58) Field of Classification Search
CPC ........... A61L 2/04; A61L 11/00; B09B 3/0083
See application file for complete search history.

(56) References Cited

U.S. PATENT DOCUMENTS

| 5,489,200 A * | 2/1996 | McGraw ............... B29B 13/022 100/246 |
| 7,204,956 B1 | 4/2007 | Beraud |
| 2003/0175410 A1* | 9/2003 | Campbell ............... A61L 27/38 427/2.24 |
| 2005/0170070 A1* | 8/2005 | Layrolle ............. A61F 2/30767 427/2.1 |
| 2011/0011141 A1* | 1/2011 | Hepburn ................... B09C 1/10 71/8 |

FOREIGN PATENT DOCUMENTS

| GB | 2465144 A | 5/2010 |
| WO | 9911299 A1 | 3/1999 |

* cited by examiner

*Primary Examiner* — Jill Warden
*Assistant Examiner* — Matthew Krcha
(74) *Attorney, Agent, or Firm* — Andrew W. Chu; Craft Chu PLLC

(57) ABSTRACT

The method for the heat treatment of waste includes introducing the waste by into a bag and placing the bag inside an apparatus for treating waste, the apparatus including a cylindrical barrel, a removable closure lid and a bottom moveable inside the barrel, at least in the direction of the lid. After the bag has been placed in the apparatus heat treatment of waste is carried out by raising the temperature of the lid and the bottom and by providing this lid and this bottom with a hold temperature. At least during the rise in temperature of the lid and the bottom, and before the hold temperature is reached, this lid and this bottom are moved towards each other at least once. A temperature conferred on the lid differs by at most 2° C. from the temperature of the bottom.

8 Claims, 4 Drawing Sheets

METHOD AND APPARATUS FOR HEAT TREATMENT OF WASTE

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

This invention relates to a method for heat treatment of waste as well as an apparatus for implementing this method.

This invention concerns the field of waste treatment, more particularly that of the treatment of waste by heat, inside a heated chamber. This invention will have applications most particularly, but by no means limitatively, in the treatment of household, hospital or biohazardous waste.

2. Description of Related Art Including Information Disclosed Under 37 CFR 1.97 and 37 CFR 1.98.

Waste treatment methods of this type are already known, which consist of introducing waste into a bag before placing inside an apparatus designed to treat such waste a load consisting of the bag and the waste contained therein.

The method then consists, after placing the load inside the apparatus, of raising the temperature of the bottom and of the lid and then applying a hold temperature to this bottom and this lid, and therefore the load. Moreover, before this hold temperature is reached, the bottom and the lid are moved towards each other at least once and the load may be compacted.

For the implementation of the method, an apparatus is used, in particular one such as that described in U.S. Pat. No. 7,204,956, comprising a bottom and a lid incorporating heating means, which lead to an inhomogeneity of temperature inside the load. This inhomogeneity leads to the inhomogeneous and/or incomplete treatment of the waste (which is not acceptable for hospital or biohazardous waste) or requires, for an appropriate treatment of such waste, that the duration of the implementation of the method be extended substantially, which entails the consumption of a considerable amount of energy.

Moreover, this method consists of moving the bottom and the lid towards each other, and even compacting the load. Now, when the load contains a non-compactable object, the movement of the bottom and the lid towards each other is interrupted and the load is directly subjected to the hold temperature. The interruption of this movement of the bottom and of the lid leads to insufficient compaction of the load, which once again leads to an inhomogeneity of temperature inside this load with the same consequences as described above.

Furthermore and in spite of the movement of the bottom and the lid towards each other, the load usually contains a certain quantity of residual air, which causes poor conduction of the heat and therefore an inhomogeneity of temperature inside the load, again with the same consequences as described above.

Finally, the method involves allowing the air to be evacuated out of the apparatus, which then includes a filter designed to filter said evacuated air. Now, such a filter is particularly sensitive to the presence of liquids in the evacuated air, water in particular, which will render said filter totally inactive and will require it to be cleaned, and even removed. In order to overcome this drawback, the apparatus is equipped with means designed to detect the presence of such a liquid and to interrupt the waste treatment process if such a liquid is detected. Given that most waste will contain such a liquid, either the treatment of this waste will be rapidly interrupted, or the time during which the load is heated will have to be extended significantly, which, once again, will entail the consumption of a considerable amount of energy.

SUMMARY OF THE INVENTION

This invention seeks to overcome the drawbacks of the methods known in the prior art consisting of treating waste and the apparatus for implementing such methods.

To this effect, the invention concerns a method for the heat treatment of waste, which method consists of:
  introducing the waste to be treated into a bag;
  placing the bag containing the waste inside an apparatus designed to treat said waste, and comprising a cylindrical barrel, a removable closure lid for this cylindrical barrel, and a bottom movable inside the cylindrical barrel, at least in the direction of the lid;
  after placing the bag containing the waste inside the apparatus:
  carrying out heat treatment of this waste is carried, first of all by raising the temperature of the lid and of the bottom of the apparatus and then by applying a hold temperature to the lid and bottom;
  at least during the rise in temperature of the lid and of the bottom and before reaching the hold temperature, moving this lid and this bottom towards each other at least once.

This method is characterized by conferring on the lid, or the bottom, a temperature that differs by at most 2° C. from the temperature of the bottom, or of the lid, at least during the time the hold temperature is maintained.

This method also involves, before the hold temperature is reached and after moving the bottom and the lid towards each other at least once, moving this bottom and this lid away from each other and then towards each other once more.

Another characteristic of this method consists, before applying said hold temperature to the bottom and to the lid, of measuring the distance between the bottom and the lid, either to apply the said hold temperature when this distance is less than a given value, or to interrupt the process when this distance is greater than this given value.

An additional characteristic consists of filtering, with a filter that is part of the apparatus, the air evacuated out of the apparatus and heating this filter to a temperature allowing the liquid contained in the evacuated air to be vaporized.

The invention also relates to an apparatus for treating waste comprising a chamber intended to receive the waste to be treated, comprising a cylindrical barrel, a removable closure lid for this cylindrical barrel, and a bottom movable inside this cylindrical barrel, at least in the direction of the lid.

This treatment apparatus is characterized by the fact that it comprises means for conferring on the lid, or on the bottom, a given temperature that differs by at most 2° C. from the temperature of the bottom, or the lid.

A further characteristic consists in that the means for conferring a given temperature on the lid, or on the bottom, comprise:

at least a means for reading at least the temperature of this lid, or this bottom;
at least a means for heating this lid, or this bottom;
at least a means for cooling this lid, or this bottom;
means for controlling the means for heating this lid, or this bottom, and the means for cooling this lid, or this bottom, at least depending on the given temperature and the temperature of this lid, or this bottom, read.

Thus, the method according to the invention consists of conferring on the bottom, or on the lid, a temperature that differs by at most 2° C. from the temperature of the lid, or the bottom, at least during the time the hold temperature is maintained. Such a characteristic allows, advantageously, a homogeneous temperature to be established inside the load, which leads to the homogeneous and complete treatment of the waste.

Moreover, and in a particularly surprising way, conferring on the bottom, or the lid, a temperature that differs by at most 2° C. from the temperature of the lid, or of the bottom, at least during the time the hold temperature is maintained, allows the length of time this hold temperature is maintained to be reduced considerably, and therefore also the duration of the waste treatment cycle, which is divided at least by four.

Moreover, before the hold temperature is reached and after moving the bottom and the lid towards each other at least once, the method involves moving this bottom and this lid away from each other and then towards each other once more. This moving apart/moving together ensures, advantageously, that there is no more air inside the load, which contributes to establishing a homogeneous temperature inside the load.

A further characteristic involves, before applying said hold temperature to the bottom and to the lid, measuring the distance between the bottom and the lid, either to apply said hold temperature when this distance is less than a given value, or to interrupt the process when this distance is greater than this given value. This characteristic makes it possible, advantageously, to treat the waste only when the bottom and the lid are close enough to each other to guarantee a homogeneous temperature inside the load.

Furthermore, the air discharged from the apparatus is filtered and this filter is heated to a temperature allowing the liquid (more particularly the water) contained in the air to be vaporized, which makes it possible, advantageously, on the one hand, to avoid the presence of liquid in the filter and therefore to preserve the filtration properties and the effectiveness of the filter and, on the other hand, to evacuate as much of the liquid contained in the load as possible. By evacuating this liquid, the quantity of liquid inside the load is minimized, which makes it possible, advantageously, due to the low compressibility of such a liquid, to improve the compaction rate of the load and therefore to minimize the volume of the load. This makes it possible to maximize the movement of the bottom and the lid towards each other and therefore to improve the homogeneity of the temperature inside the load, and thus the treatment of the waste.

Finally, each of these characteristics makes it possible, advantageously, to optimize the treatment of the waste, to shorten the time needed to treat the waste and thus to make substantial energy savings.

Other purposes and benefits of this invention will become clear in the course of the description that follows relating to the embodiments, which are given by way of indicative but not limitative examples.

BRIEF DESCRIPTION OF THE DRAWINGS

The comprehension of said description will be facilitated by referring to the drawings enclosed.

DETAILED DESCRIPTION OF THE DRAWINGS

Figure 1:
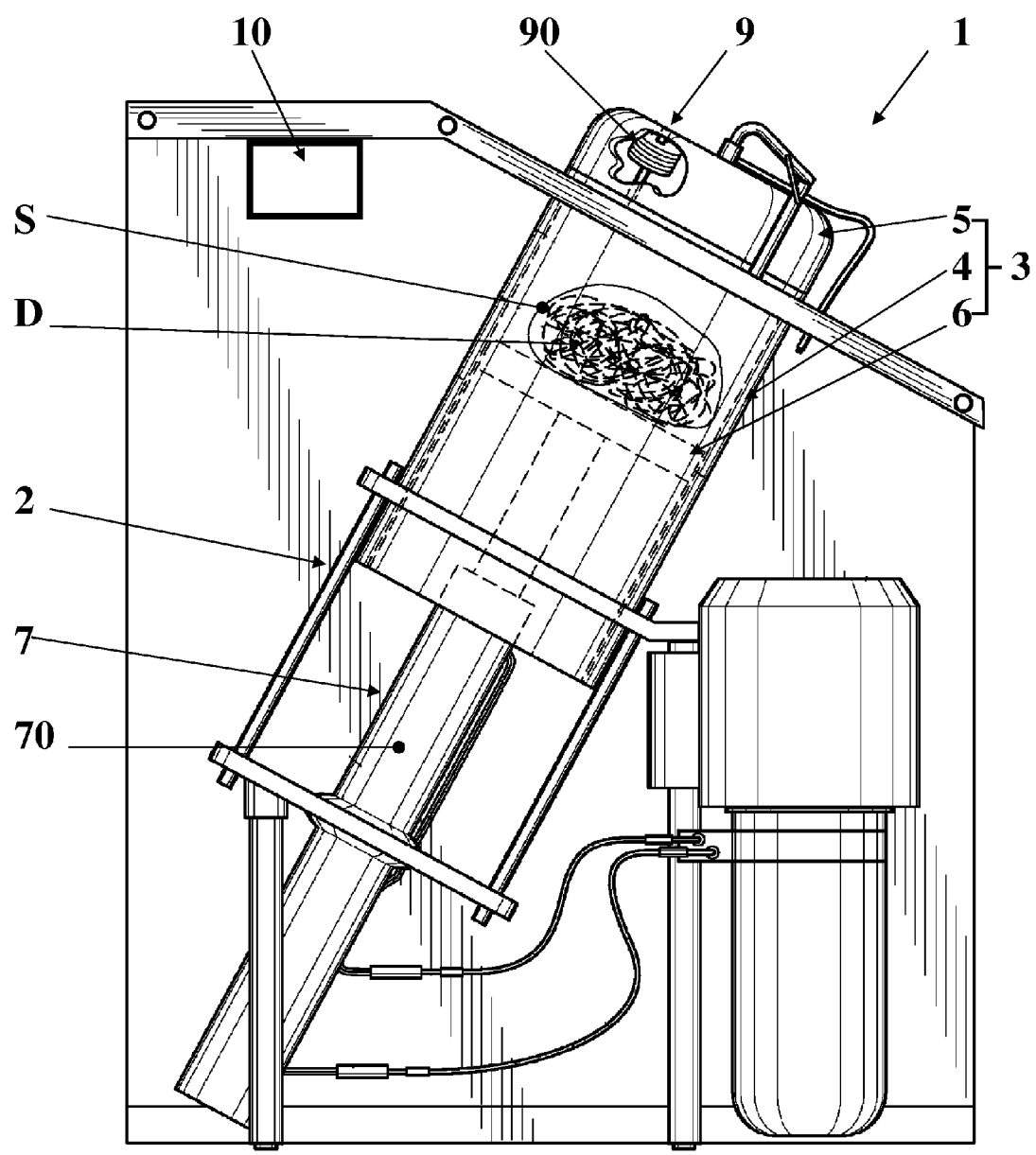
FIG. 1 is a schematic side view, in partial cross section, of the waste treatment apparatus according to the invention.
Figure 2:
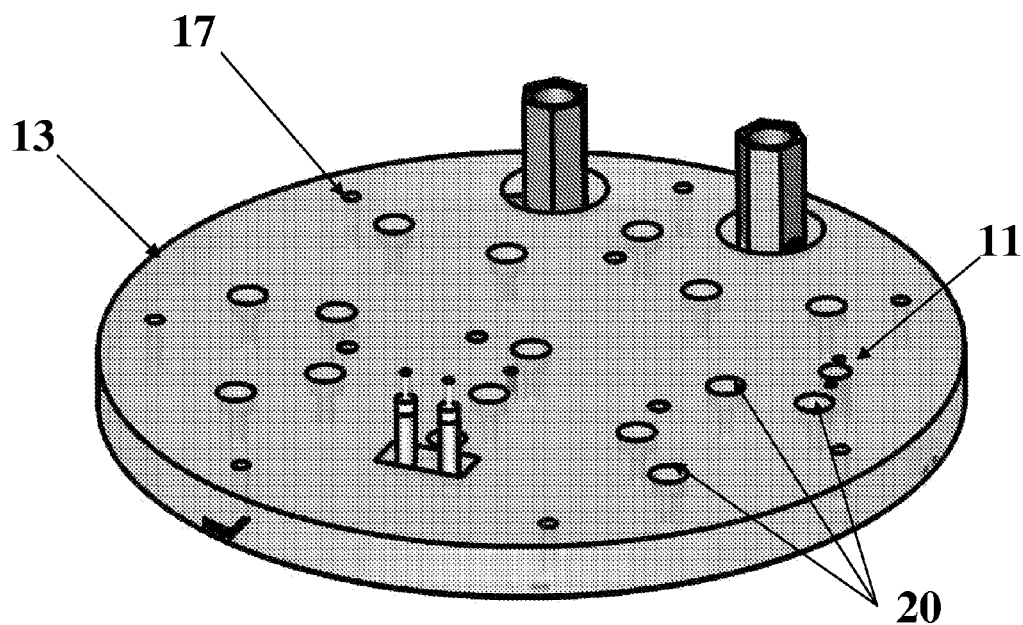
FIG. 2 is a schematic perspective view of a thermal block which is part of the bottom or the lid of the apparatus shown in FIG. 1.
Figure 3:
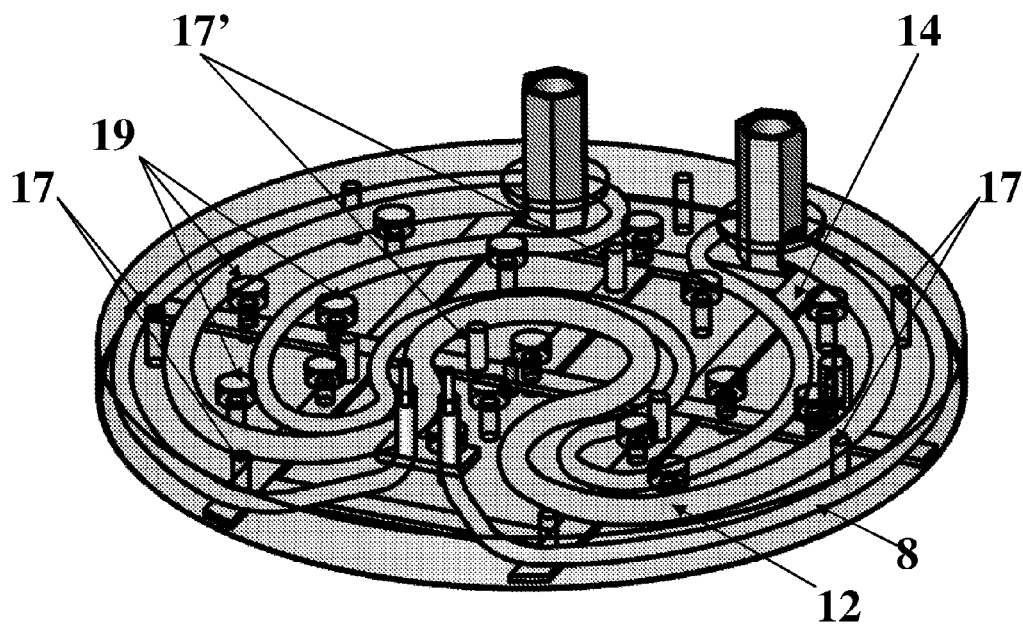
FIG. 3 is a schematic perspective view, similar to FIG. 2 showing the layout of the different components inside the thermal block.
Figure 4:
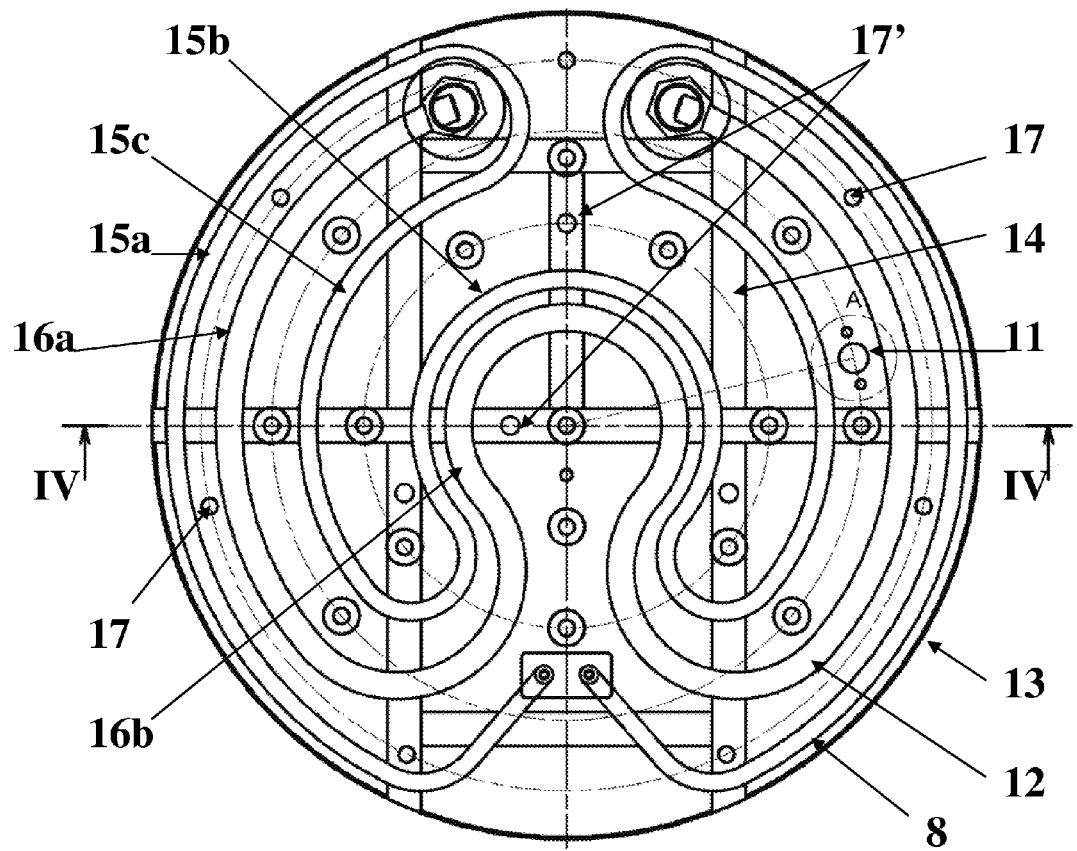
FIG. 4 is a schematic view from above of the layout of the different components in the thermal block.
Figure 5:
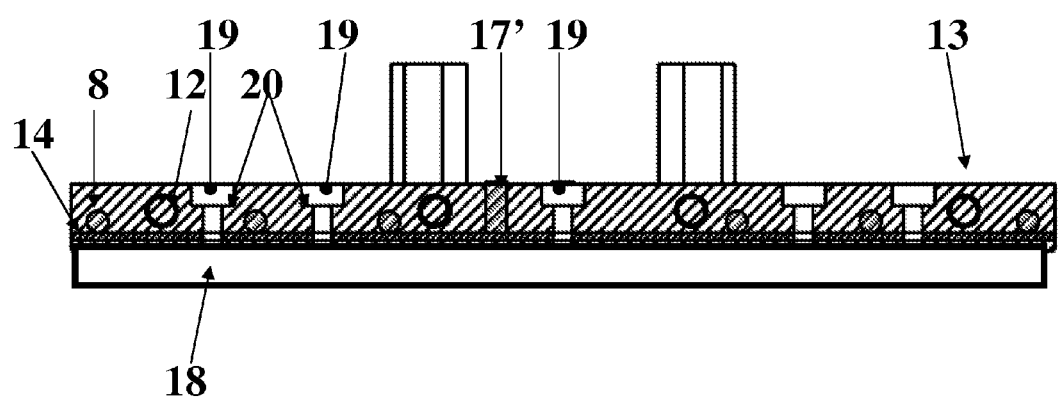
FIG. 5 is a schematic view in cross section along the line IV-IV of the thermal block shown in FIG. 4.
Figure 6:
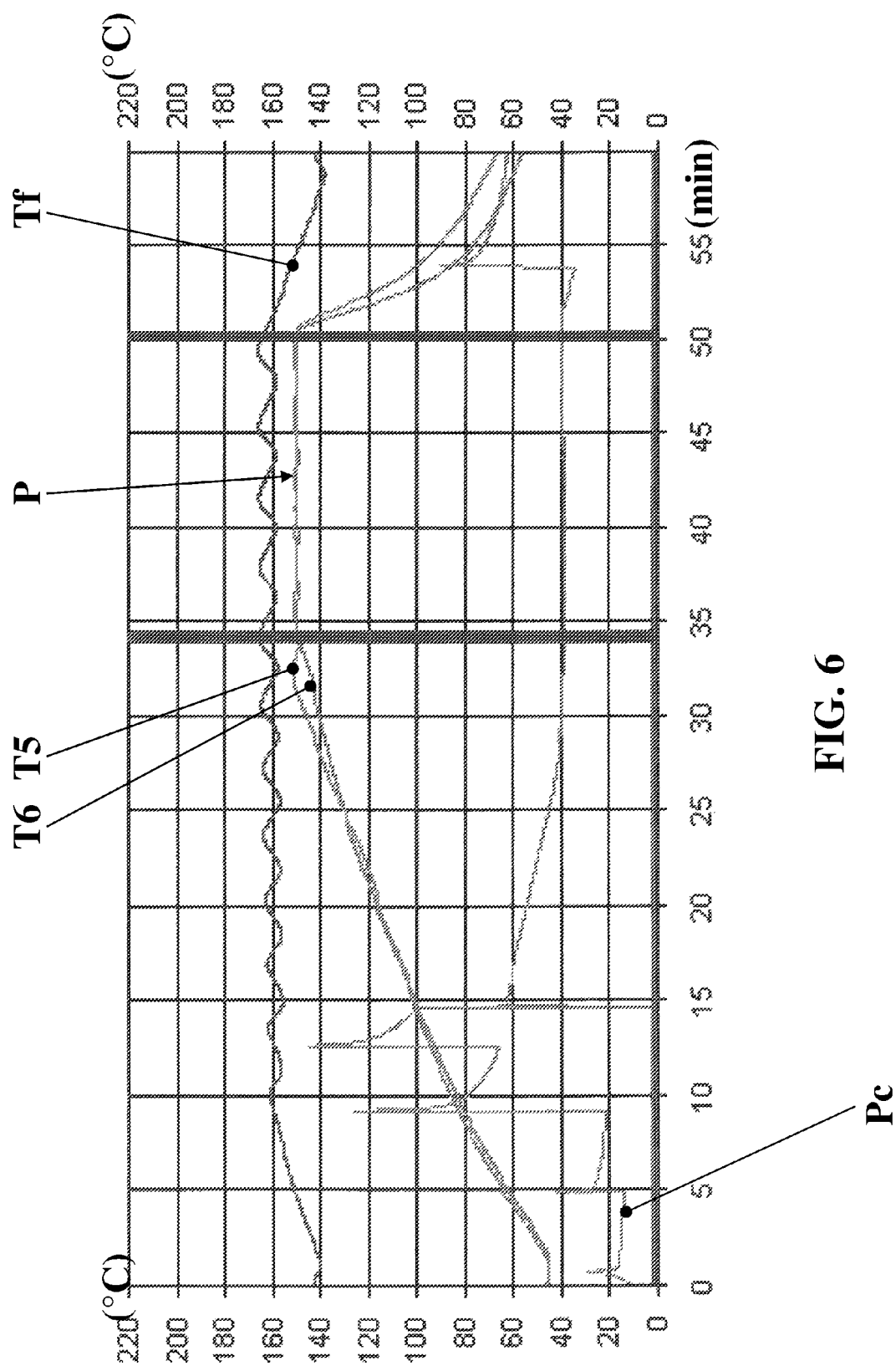
FIG. 6 is a graph illustration showing the changes over time in different parameters (temperature of the bottom, temperature of the lid, temperature of the filter, pressure inside the load) during the implementation of the method according to the invention.

This invention concerns the field of waste treatment, more particularly that of the treatment of waste by heat, inside a heated chamber.

The invention concerns then a method of heat treating (and more particularly disinfecting) waste, in particular biohazardous, hospital or household waste.

The invention also concerns an apparatus 1 for treating waste D, designed more particularly to implement the aforementioned treatment method.

In a known manner, an apparatus 1 for treating waste D comprises a chassis 2 and a chamber 3, mounted on this chassis 2, inside which the heat treatment of the waste D takes place.

This chamber 3 comprises a cylindrical barrel 4, defined by an internal wall, and extending along an axis at an angle preferably between 45 and 90° inclusive from horizontal.

This chamber 3 also comprises a lid 5 for closing the cylindrical barrel 4 and therefore this chamber 3. The lid is 5 of the removable type to allow access to the inside of the cylindrical barrel 4 and it is mounted hinged onto the chassis 2, between an open position and a closed position of this barrel 4.

This chamber 3 also comprises a bottom 6, positioned inside the cylindrical barrel 4, and slidingly movable inside this cylindrical barrel 4, at least in the direction of the lid 5.

The apparatus 1 for treating waste D further comprises means 7 for driving the movement of the bottom 6 of the chamber 3.

Such drive means 7 comprise a cylinder 70 interposed between this bottom 6 and the chassis 2. This cylinder 70 may be electric, pneumatic, or preferably, hydraulic. In the case of a pneumatic or hydraulic type cylinder 70, the apparatus 1 also comprises (more particularly fixed on the chassis 2), means for supplying this cylinder 70 with (pneumatic or hydraulic) fluid.

This treatment apparatus 1 also comprises means 8 for heating the lid 5 and means 8 for heating the bottom 6.

Moreover, this treatment apparatus 1 comprises means 9 for evacuating the air out of the chamber 3.

These means 9 for evacuating the air comprise a valve, more particularly a solenoid valve, designed to close these means 9 for evacuating the air and, therefore to prevent the evacuation of the air, more particularly in the event of liquid (in particular water) being detected during the course of a waste D treatment process.

Moreover, these means 9 for evacuating the air comprise a filter 90 designed to filter the air discharged from the chamber 3. Such a filter 90 will preferably be of the hydrophobic type.

Finally, the apparatus 1 comprises means 10 for controlling the operation of this apparatus 1, more particularly at least the means 8 for heating the lid 5 and the bottom 6 as well as the means 7 for driving the movement of this bottom 6.

These means 10 for controlling the apparatus 1 comprise a processing means (more particularly in the form of a piece of software) designed to have this apparatus 1 execute a succession of steps in a waste D treatment process.

These means 10 for controlling the apparatus 1 further comprise a memory incorporating at least a succession of steps corresponding to at least one waste D treatment process.

Finally, these means 10 for controlling the apparatus 1 comprise an interface by means of which a user of the apparatus 1 can control the execution of the different steps in such a waste D treatment process and/or select the parameters of these different steps.

According to the invention, this apparatus comprises means for conferring on the lid 5, or the bottom 6, a given temperature that differs by at most 2° C. from the temperature of the bottom 6, or of the lid 5.

In fact, these means are preferably designed to confer on this lid 5, or the bottom 6, a given temperature that differs by at most 1° C. from the temperature of the bottom 6, or the lid 5.

In this respect, it should be noted that the means for conferring a given temperature on the lid 5, or the bottom 6, comprise at least a means 11 for reading at least the temperature of this lid 5, or this bottom 6.

In a particular embodiment, these means for conferring a given temperature on the lid 5, or on the bottom 6, further comprise at least one means 11 for reading at least the temperature of the bottom 6, or the temperature of the lid 5.

Such a means 11 for reading the temperature will preferably consist of a probe or similar.

The means for conferring a given temperature on the lid 5, or on the bottom 6, further comprise at least one means 8 for heating this lid 5, or this bottom 6.

Such a means 8 for heating will consist more particularly of at least one resistor, in particular an electric resistor.

The means for conferring a given temperature on the lid 5, or on the bottom 6, also comprise at least one means 12 for cooling this lid 5, or this bottom 6.

In fact, such a means 12 for cooling will consist more particularly of a pipe inside which a heat transfer fluid circulates.

Finally, the means for conferring a given temperature on the lid 5, or the bottom 6, comprise means 10 for controlling the means 8 for heating this lid 5, or this bottom 6, as well as the means 12 for cooling this lid 5, or this bottom 6, at least depending on the given temperature and the temperature of this lid 5, or this bottom 6, read.

In a particular embodiment, these means 10 for controlling the means 8 for heating this lid 5, or this bottom 6, as well as the means 12 for cooling this lid 5, or this bottom 6, may, in an alternative or complementary way, be designed to control these means (8; 12) depending on the given temperature and the temperature of the bottom 6, or the lid 5, read.

To achieve this, the means for conferring a given temperature on the lid 5, or on the bottom 6, comprise at least one means for reading the temperature of the bottom 6, or the lid 5.

In such a case, the given temperature may consist of the temperature of the bottom 6, or the lid 5, read.

As mentioned above, the means for conferring a given temperature on the lid 5, or on the bottom 6, comprise on the one hand, at least a means 8 for heating this lid 5, or this bottom 6, and, on the other hand, at least a means 12 for cooling this lid 5, or this bottom 6.

The presence of such a heating means 8 and such a cooling means 12 in the lid 5, or in the bottom 6, makes it possible, advantageously, to create a synergy between these means (8; 12) leading to a particularly precise regulation of the temperature, increased accuracy of the temperature (of the lid 5, or of the bottom 6) as well as the exactness of the temperature (of the lid 5, or of the bottom 6), in relation to the given temperature.

According to another characteristic of the invention, the lid 5, or the bottom 6, comprises a thermal block 13 incorporating at least a means 8 for heating this lid 5, or this bottom 6, as well as a means 12 for cooling this lid 5, or this bottom 6.

In fact, this thermal block 13 is preferably made of a cast material.

In such a case, at least a heating means 8 and at least a cooling means 12 are at least partly embedded in the material of this thermal block 13, which has a melting point lower than that of such a heating means 8 and that of such a cooling means 12.

In this respect, it should be noted that, in a particular embodiment of the invention, the material of the thermal block 13 consists of aluminum, the material of the heating means 8 (more particularly a resistor) consists of copper whilst the material of the cooling means 12 (more particularly a pipe containing a heat transfer fluid) consists of a chromium-molybdenum alloy.

Another characteristic involves the thermal block 13 comprising a reinforcement 14, embedded in the material of the thermal block 13, and on which 14 rest and/or to which 14 are rendered integral at least a heating means 8 and/or at least a cooling means 12.

The presence of such a reinforcement 14 and its combination with such a heating means 8 and/or such a cooling means 12 makes it possible, advantageously, to position these means (8; 12) appropriately inside the thermal block 13, at the time of manufacturing the latter 13, and more particularly at the time of casting the material of this thermal block 13.

A further characteristic consists of the heating means 8, or the cooling means 12 comprising at least one portion interposed between two portions of the cooling means 12, or the heating means 8.

Such an embodiment makes it possible, advantageously, to regulate in an optimum manner the temperature in the vicinity of such a portion of the heating means 8, or the cooling means 12.

In a preferred embodiment, the heating means 8 and the cooling means 12 extend substantially in a plane and are arranged so as to define a loop (15; 16). In such a case, at least a part of the loop 15 in the heating means 8, or a part of the loop 16 in the cooling means 12, lies inside at least a part of a loop (16; 15) in the cooling means 12, or in the heating means 8.

More particularly, the heating means 8 and the cooling means 12 extend substantially in a plane and are arranged so as to define at least one external loop (15a; 16a) as well as at least one internal loop (15b; 16b) connected to the external loop (15a; 16a). in such a case, a loop 15 in the heating means 8, or a loop 16 in the cooling means, is interposed between an external loop (16a; 15a) and an internal loop (16b; 15b) in the cooling means 12, or in the heating means 8.

As can be seen in the figures enclosed, the heating means 8 extends substantially in a plane and is arranged so as to define an external loop 15a, an internal loop 15b, and an intermediate loop 15c connected to the external loop 15a and to the internal loop 15b.

As for the cooling means 1, the latter comprises, on the one hand, an external loop 16a interposed between the external 15a and intermediate 15c loops of the heating means 8, and on the other hand, an internal loop 16b lying inside the internal loop 15b of this heating means 8.

An additional characteristic consists of the thermal block 13 comprising means 17 for positioning at least one heating means 8, or at least one cooling means 12, in relation to the reinforcement 14 and/or in relation to at least one cooling means 12, or in relation to at least one heating means 8.

This thermal block 13 may also comprise means 17' for positioning said reinforcement 14, inside a mold in which the material intended to constitute said thermal block 13 is cast.

In fact, these positioning means (17; 17') are, more particularly, designed to position a reinforcement 14, a heating means 8 and/or a cooling means 12, inside a mold in which the material intended to constitute said thermal block 13 is cast and in the final position they take up inside this thermal block 13.

As can be seen in the figures enclosed, these positioning means (17; 17') take the form of a stud or similar, which can be rendered integral with the reinforcement 14 and extends out of this reinforcement 14, in particular in a perpendicular manner.

According to another characteristic of the invention, the lid 5, or the bottom 6, comprises a plate 18 made of non-oxidizing material, positioned inside the cylindrical barrel 4, comprising an inner surface facing the bottom 6, or the lid 5, as well as an outer surface facing, on the one hand, in the opposite direction to that of the bottom 6, or the lid 5, and, on the other hand, facing the thermal block 13 that is part of this lid 5, or of this bottom 6, and which is rendered integral with this plate 18 made of a non-oxidizing material.

According to an additional characteristic, the non-oxidizing plate 18 that is part of the bottom 6 has dimensions (more particularly a diameter) which, in relation to the internal dimensions of the cylindrical barrel 4, are defined so as to allow this bottom 6 to move without friction inside this cylindrical barrel 4.

Another characteristic consists of the lid 5, or the bottom 6, comprising means 19 for fastening the plate 18 made of a non-oxidizing material onto the thermal block 13.

In fact, such fastening means 19 consist of screws that pass through an opening 20 in the thermal block 13, and cooperate with an internal thread in the plate 18 made of a non-oxidizing material.

An additional characteristic consists of the lid 5, or the bottom 6, comprising means 19 for adjusting the position of this plate 18 made of a non-oxidizing material in relation to the thermal block 13.

The presence of these adjusting means makes it possible, advantageously, to optimize the flatness of the plate 18 made of a non-oxidizing material.

Additionally, the lid 5, or the bottom 6, comprises means for creating a thermal bridge between the plate 18 made of a non-oxidizing material and thermal block 13.

In this respect, it will be noted that the adjusting means and/or the means for creating a thermal bridge may, at least partly, consist of the means 19 for fastening the plate 18 made of a non-oxidizing material onto the thermal block 13.

According to another characteristic, the treatment apparatus 1 further comprises means for guiding the linear movement of the bottom 6 in relation to the cylindrical barrel 4.

The presence of these guiding means makes it possible, advantageously, to ensure this bottom 6 makes only a linear movement inside this barrel 4 and thus to prevent the bottom 6 rotating in relation to the barrel 4 causing the blockage of this bottom 6.

In fact, in a preferred embodiment, these guiding means comprise, on the one hand, a fixed groove associated with the cylindrical barrel 4 and, on the other hand, a moving lug, associated with the bottom 6, and cooperating with said fixed groove.

Finally, the treatment apparatus 1 comprises means for determining the distance between the bottom 6 and the lid 5.

These means for determining such a distance in fact consist of means for measuring the distance between this bottom 6 and a fixed reference, which is made in the apparatus 1, and which is situated at a fixed distance from the lid 5.

In fact and in a preferred embodiment of the invention, these measuring means comprise, on the one hand, a wire attached to the bottom 6, and on the other hand, a means of winding up this wire (more particularly in the form of a reel) and also a means of measuring the length of the wire wound up/unwound (more particularly in the form of a means of counting the number of turns made by the reel).

As mentioned above, this invention also relates to a method for the heat treatment of waste D, in particular household, hospital and biohazardous waste.

This method is, more particularly (but not exclusively), implemented by the treatment apparatus 1 described above, which is, more particularly (but not exclusively) designed to implement this method.

In fact, this method for the heat treatment of waste D consists of:
 introducing the waste to be treated into a bag S;
 placing the bag S containing the waste D inside an apparatus 1 designed to treat said waste D, and comprising a cylindrical barrel 4, a removable closure lid 5 for this cylindrical barrel 4, and a bottom 6 movable inside this cylindrical barrel, at least in the direction of the lid 5;

In fact, this method consists, more particularly, of placing the bag S containing the waste D inside a chamber 3 that is part of this apparatus 1, and which comprises such a cylindrical barrel 4, such a lid 4 and such a movable bottom 6.

This method also consists, after placing the bag S of waste D inside the apparatus 1 of:
 carrying out a heat treatment of this waste D, first of all by raising the temperature of the lid 5 and the bottom 6 of the apparatus 1 and then by applying a hold temperature P to the lid 5 and bottom 6;

at least during (and even before) the rise in temperature of the lid 5 and bottom 6 and before reaching the hold temperature P, moving this lid 5 and this bottom 6 towards each other at least once.

According to the invention, this method consists of conferring on the lid 5, or the bottom 6, a temperature (T5, or T6) that differs by at most 2° C. from the temperature (T6, or T5) of the bottom 6, or the lid 5, at least during the time the hold temperature is maintained.

In fact this method consists, preferably, of conferring on the lid 5, or the bottom 6, a temperature (T5, or T6) that differs by at most 1° C. from the temperature (T6, or T5) of the bottom 6, or the lid 5, at least during the time the hold temperature is maintained.

Preferably, this method consists of conferring on the lid 5, or the bottom 6, a temperature that differs by at most 2° C. from the temperature (and preferably by at most 1° C.) from the temperature of the bottom 6, or the lid 5, during the time the hold temperature P is applied, as well as during the rise in the temperature of the lid 5 and the bottom 6.

According to another characteristic of this invention, at least during (and even before) the rise in the temperature of the lid 5 and the bottom 6 and before and before reaching the hold temperature P, the bottom 6 and the lid 5 are successively moved towards each other a number of times, without moving the bottom 6 and the lid 5 away from each other between the two successive movements towards each other.

In fact, the bottom 6 and the lid 5 are moved towards each other at least once, compressing the bag S and the waste D. Such an embodiment reduces the volume of the bag S and the waste D as well as evacuating the air contained in it.

According to another characteristic, before this movement with compression, the bottom 6 and the lid 5 are moved towards each other at least once without compressing the bag S and the waste D. Such an embodiment allows the air to be removed from the chamber 3.

An additional characteristic of this method also consists, before the hold temperature is reached and after moving the bottom 6 and the lid 5 towards each other at least once, of moving this bottom 6 and this lid 5 away from each other and then towards each other once more.

In this respect, the process according to the invention consists of such moving apart/moving together being carried out when the temperature T5 of the lid 5 and/or the temperature T6 of the bottom 6 are lower than a given value (in particular lower than 110° C., preferably lower than 100°, more particularly between 90 and 100° C. inclusive).

Such an embodiment makes it possible, advantageously, on the one hand by moving the bottom 6 away, to loosen the waste D (and even to expel the air contained in the waste D and/or in the bag S, out of this bag S, in particular by suction) and, on the other hand by moving the bottom 6 in, to optimize the evacuation of the air and to ensure that there is no longer any air inside the chamber 3, the bag S and the waste D, before applying the hold temperature P.

By reducing the quantity of air in the chamber, advantageously, it is possible to resolve at least the problems of incorrect operation, inhomogeneity of temperature and poor conduction of the temperature that occur when a hold temperature P is applied when there is still air present.

Surprisingly, by carrying out this moving away/moving together of the bottom 6 and the lid 5, the treatment of the waste is improved substantially.

In this respect, it will be noted that, in a preferred embodiment of the invention, before reaching the hold temperature P and after moving the bottom 6 and the lid 5 together at least once with compression of the bag S and the waste D with a given pressure (in particular greater than 120 bars, preferably of the order of 140 bars), we read, on the one hand, the temperature (more particularly the temperature T5 of the lid and/or the temperature T6 of the bottom 6) and, on the other hand, the pressure Pc inside the bag S and the waste D.

The method then consists of moving the bottom 6 and the lid 5 apart and then moving this bottom 6 and this lid 5 towards each other again when, on the one hand, the temperature (T5; T6) is lower than a given value (in particular lower than 110° C., preferably lower than 100°, more particularly between 90 and 100° C. inclusive) and, on the other hand, the pressure Pc inside the bag S and the waste D is greater than a given value (in particular greater than 80 bars, preferably greater than 90 bars). In fact, in these temperature and pressure conditions, it is estimated that there is still air inside the chamber 3, the bag S and/or the waste D.

In this respect, it will be noted that, when, on the one hand the temperature (T5; T6) is lower than a given value (in particular lower than 110° C., preferably lower than 100°, more particularly between 90 and 100° C. inclusive) and, on the other hand, the pressure Pc inside the bag S and the waste D is lower than a given value (in particular lower than 80 bars, preferably lower than 60 bars), the method involves applying the hold temperature P directly without carrying out a moving apart/moving in of the bottom 6, because it is estimated that there is no more air inside the chamber 3, the bag S and/or the waste D.

According to another characteristic, after moving the bottom 6 and the lid 5 towards each other once more (this further moving together following the moving apart of this bottom 6 and this lid 5), we read the pressure Pc inside the bag S and the waste D.

In such a case, when this pressure Pc is greater than a given value (in particular higher than 80 bars, preferably higher than 90 bars), the bottom 6 is moved apart/moved in once more, or the treatment process may even be interrupted, as it is estimated that there is still air inside the chamber 3, the bag S and/or the waste D.

In a preferred embodiment, the process will thus be interrupted when, after several moving apart/moving together operations, the pressure Pc is still greater than a given pressure value (in particular greater than 80 bars, preferably greater than 90 bars).

However, when this pressure Pc read is lower than a given pressure value (in particular lower than 80 bars, preferably lower than 60 bars), the process consists of continuing to increase the temperature and applying the hold temperature P (to the lid 5 and to the bottom 6), because it is estimated that there is no longer any air in the chamber 3, the bag S or the waste D.

According to an additional characteristic, when, after moving the bottom 6 out, this bottom 6 is moved in once again, this moving in is carried out so that the distance between this bottom 6 and this lid 5, after this new movement inwards, is greater than or equal to the distance between this bottom 6 and this lid 5 before moving this bottom 6 and this lid 5 apart.

In this respect, it will be noted that the outward movement of the bottom 6 takes place over a travel of between 2 and 10 mm inclusive, preferably of the order of 4 mm.

As mentioned above, this movement inwards is carried out so that the distance between this bottom 6 and this lid 5, after this new moving together, is higher than or equal to the distance between this bottom 6 and this lid 5 before moving this bottom 6 and this lid 5 apart.

In this respect, it will be noted that this distance is, in fact, determined so that the load (bag S and waste D contained in this bag S) is in contact with the lid 5 and the bottom 6. This allows for better conduction of the heat between, on the one hand, the lid 5 and the waste D and, on the other hand, the bottom 6 and the waste D, which greatly improves the treatment of said waste D. This distance may also be determined so that the waste D is loose inside the bag S and is not under pressure when the hold temperature P is applied. Surprisingly, this characteristic improves the treatment of the waste.

According to another characteristic of the invention, before applying the hold temperature P to the lid 5 and to the bottom 6, we measure the distance between the bottom 6 and the lid 5, either to apply said hold temperature P when this distance is less than a given value, or to interrupt the process when this distance is greater than this given value.

It will be noted that the given value determined for this distance is less than or equal to 100 mm, preferably of the order of 50 mm.

Such a characteristic makes it possible, advantageously, to apply a hold temperature P only when the distance is less than a given value, that is to say only when the load (bag and waste contained in this bag) has a thickness less than a given value. This characteristic makes it possible, advantageously, to improve the heat conduction and the temperature homogeneity inside the load and thus to ensure appropriate treatment of the waste.

An additional characteristic of the method involves allowing the evacuation of the air contained in this apparatus 1 (more particularly contained in the chamber 3, the bag S and/or the waste D) out of the apparatus 1, and more particularly out of the chamber that is part of this apparatus 1.

In fact, the evacuation of the air is allowed by means 9 of evacuating the air mentioned above, at least during the rise in temperature and/or at least during at least one moving together of the lid 5 and the bottom 6.

This characteristic makes it possible, once again, to improve the heat conduction and the temperature homogeneity inside the load.

According to the invention, the evacuation of the air is prevented while the hold temperature P is being applied to the lid 5 and the bottom 6, by closing the valve in the means 9 for evacuating the air.

Moreover, this method involves filtering the air evacuated out of the apparatus 1, more particularly out of the chamber 3 that is part of the apparatus 1. Such filtration is done by a filter 90 that is part of the apparatus 1, and more particularly part of the means 9 for evacuating the air from this apparatus 1.

An additional characteristic involves heating this filter 90 to a temperature Tf enabling the liquid contained in the air evacuated to be vaporized.

In this respect, it will be noted that this temperature Tf is higher than 90° C., preferably higher than 140° C.

Such heating is preferably done as soon as the waste D treatment process according to the invention is started.

Such heating makes it possible, advantageously, to vaporize the liquid (in particular the water) contained in the air and thus to avoid such liquid polluting the filter 90 and rendering it ineffective.

Another characteristic of the method involves detecting the presence of a liquid (more particularly in the means 9 for evacuating the air) and, if such a liquid is detected, of preventing the evacuation of the air (by closing the valve in the means 9 for evacuating the air) and/or by moving the bottom 6 and the lid 5 together, or even by interrupting the waste D treatment process.

As mentioned above, the air evacuated is filtered by a heated filter 90, which substantially reduces the likelihood of detecting such a liquid, so that the likelihood of interrupting the waste D treatment process according to the invention is considerably less compared to the methods known in the prior art. The implementation of the method according to the invention makes it possible, advantageously, to increase the likelihood of completing the waste D treatment process, in comparison to the processes known in the prior art.

As mentioned above, the method consists of applying a hold temperature P to the lid 5 and to the bottom 6. In fact, whilst this temperature P is maintained, the temperature of this lid 5 and the temperature of this bottom 6 are between 140° and 160° C. inclusive, preferably of the order of 150° C. A preferred embodiment of the invention involves, while this hold temperature P is maintained, the temperature T5 of this lid 5 and the temperature T6 of this bottom 6 being between 155° and 158° C. inclusive, preferably between 156° and 157° C. inclusive.

In fact, such a hold temperature P is applied for a length of time between 10 and 30 minutes inclusively, preferably of the order of 15 minutes.

After this hold temperature P has been applied, the method involves calculating the delta pressure between the beginning of the heating and the end of the hold temperature P. When this delta is greater than a given value (between 3.5 and 5 bars inclusively, preferably of the order of 4.2 bars), the waste D is considered as treated. However, if this delta is lower than a given value, the waste is considered as untreated. In this respect, it will be noted that this given delta value corresponds, in fact, to the pressure at which there is a break in the waste's DNA.

The method according to the invention involves, after applying a hold temperature P to the 5 and to the bottom 6, cooling this lid 5 and this bottom 6, using the means 12 for cooling this lid 5 and this bottom 6.

Additionally, when, during the cooling of the lid 5 and the bottom 6, the temperature of this lid 5 and/or this bottom 6 reaches a given value (between 80° C. and 95° C. inclusive, preferably of the order of 90° C.), the bottom 6 and the lid 5 may be moved together, more particularly to compact the load, under a pressure of between 80 and 100 bars inclusive, preferably of the order of 90 bars. This makes it possible, advantageously, to obtain a neatly formed disk of waste.

The method then involves continuing to cool the lid 5 and the bottom 6 so that, when the temperature of this lid 5 and/or of this bottom 6 reaches a given value (between 50° C. and 70° C. inclusive, preferably of the order of 60° C.), the valve in the means 9 for evacuating the air can be opened.

Finally, at a given lid 5 and/or bottom 6 temperature (preferably lower than) 50°, the lid 5 can be opened.

I claim:

1. A method for heat treatment of waste, comprising the steps of:
    introducing waste into a bag;
    placing the bag containing the waste inside an apparatus to treat said waste, said apparatus being comprised of a cylindrical barrel, a removable closure lid-for said cylindrical barrel, and a bottom movable inside said cylindrical barrel, at least in a direction of relative to the lid;

raising temperature of the lid and the bottom of the apparatus;

applying a hold temperature to the lid and the bottom;

moving the lid and the bottom toward each other at least once during the step of raising temperature of the lid and bottom and before the step of applying the hold temperature, wherein a temperature conferred on the lid differs by at most 2° C. from a temperature of the bottom, during the step of applying the hold temperature; and moving said bottom and said lid away from each other and then towards each other once more, before the hold temperature is reached and after moving the bottom and the lid towards each other at least once.

2. The method for heat treatment of waste according claim 1, further comprising the step of:

lowering temperature of a remaining one of said pair of end parts, said one of said pair being heated during the step of raising temperature, said remaining one of said pair being cooled during the step of lowering temperature, wherein at least one of said lid hold temperature and said bottom hold temperature is a given cooled temperature after the step of lowering temperature;

measuring said given heated temperature and said given cooled temperature so as to determine a measured heated temperature and a measured cooled temperature, respectively; and controlling the step of raising temperature and the step of lowering temperature according to said measured heated temperature and said measured cooled temperature.

3. The method for heat treatment of waste, according to claim 1, wherein the step of moving the lid and said bottom together at least once comprises compressing the bag and the waste.

4. The method for heat treatment of waste, according to claim 1, wherein the bottom and the lid are moved towards each other again so that distance between said bottom and the lid, after being moved together, is greater than or equal to distance between said bottom and the lid before moving said bottom and the lid away from each other.

5. The method for heat treatment of waste, according to claim 1, wherein, after moving the bottom and the lid towards each other once more, the pressure inside the bag and the waste is read, either to continue raising the temperature and apply the hold temperature when the pressure read is lower than a given pressure value, or to move the bottom and the lid away from each other/towards each other once more when said pressure is greater than said given pressure value, or even to interrupt the treatment.

6. The method for heat treatment of waste, according to claim 1, further comprising:

measuring a distance between said bottom and the lid so as to determine a measured distance value before the step of applying the lid hold temperature;

initiating the step of applying the lid hold temperature when said measured distance value is less than a given distance value; and interrupting the step of applying the lid hold temperature when said measured distance value is greater than said given distance value.

7. The method for heat treatment of waste, according to claim 1, further comprising the step of:

evacuating air out of the apparatus during at least one step selected from the group consisting of the step of raising temperature and the step of moving the lid and said bottom.

8. A method for heat treatment of waste, comprising the steps of:

introducing waste into a bag;

placing the bag containing the waste inside an apparatus to treat said waste, said apparatus being comprised of a cylindrical barrel, a removable closure lid-for said cylindrical barrel, and a bottom movable inside said cylindrical barrel, at least in a direction of relative to the lid;

raising temperature of the lid and the bottom of the apparatus;

applying a hold temperature to the lid and the bottom;

moving the lid and the bottom toward each other at least once during the step of raising temperature of the lid and bottom and before the step of applying the hold temperature, wherein a temperature conferred on the lid differs by at most 2° C. from a temperature of the bottom, during the step of applying the hold temperature;

reading temperature and pressure inside the bag so as to determine a measured temperature value and a measured pressure value, respectively, before reaching said given heated temperature in the step of raising temperature and after moving the bottom and the lid towards each other at least once with compression of the bag and the waste; and moving the bottom and the lid away from each other and then towards each other once more, when said temperature value is lower than a given temperature value and when said measured pressure is greater than a given pressure value.

* * * * *